(12) United States Patent  
Fukutomi et al.

(10) Patent No.: US 8,100,014 B2  
(45) Date of Patent: Jan. 24, 2012

(54) ULTRASONIC FLAW DETECTION APPARATUS AND ULTRASONIC FLAW DETECTION PROGRAM

(75) Inventors: Hiroyuki Fukutomi, Tokyo (JP); Shan Lin, Tokyo (JP)

(73) Assignee: Central Research Institute of Electric Power Industry, Chiyoda-Ku, Tokyo (JP)

( * ) Notice: Subject to any disclaimer, the term of this patent is extended or adjusted under 35 U.S.C. 154(b) by 373 days.

(21) Appl. No.: 12/300,417

(22) PCT Filed: May 23, 2007

(86) PCT No.: PCT/JP2007/000553  
§ 371 (c)(1),  
(2), (4) Date: Nov. 11, 2008

(87) PCT Pub. No.: WO2007/135782  
PCT Pub. Date: Nov. 29, 2007

(65) Prior Publication Data  
US 2009/0308163 A1    Dec. 17, 2009

(30) Foreign Application Priority Data  
May 23, 2006 (JP) ................................ 2006-143394

(51) Int. Cl.  
*G01N 29/07* (2006.01)
(52) U.S. Cl. ................ 73/598; 73/602; 73/627
(58) Field of Classification Search .............. 73/598, 73/600, 602, 622, 627  
See application file for complete search history.

(56) References Cited

U.S. PATENT DOCUMENTS

| | | | | | |
|---|---|---|---|---|---|
| 3,996,791 | A | * | 12/1976 | Niklas et al. | 73/602 |
| 3,996,792 | A | * | 12/1976 | Kubota et al. | 73/611 |
| 4,238,725 | A | * | 12/1980 | Karplus et al. | 324/727 |
| 4,679,437 | A | * | 7/1987 | Koike et al. | 73/622 |
| 5,839,635 | A | * | 11/1998 | Mansfield et al. | 225/96.5 |
| 2009/0007678 | A1 | | 1/2009 | Fukutomi et al. | |

FOREIGN PATENT DOCUMENTS

| | | |
|---|---|---|
| JP | 2-78949 A | 3/1990 |
| JP | 5-61590 B2 | 9/1993 |
| JP | 6-60894 B2 | 8/1994 |
| JP | 11-23539 A | 1/1999 |
| JP | 11-183452 A | 7/1999 |
| JP | 2002-62281 A | 2/2002 |

(Continued)

OTHER PUBLICATIONS

International Search Report, PCT/2007/000553, Aug. 15, 2007.

(Continued)

*Primary Examiner* — J M Saint Surin  
(74) *Attorney, Agent, or Firm* — Notaro, Michalos & Zaccaria P.C.

(57) ABSTRACT

A plurality of ultrasonic flaw detection methods can be switched and executed by a simple operation. An ultrasonic flaw detection apparatus includes a switching circuit 3 for permitting an angle probe 1 and a normal probe 2 to be arbitrarily switched to a transmission unit T and a reception unit R of a flaw detector. The switching circuit 3 can select an angle flaw detection mode for transmitting and receiving an ultrasonic beam only by the angle probe, an SPOD mode for transmitting the ultrasonic beam by the angle probe and receiving a diffracted wave by the normal probe and a flaw detection mode executed by a combination of angle flaw detection mode.

11 Claims, 11 Drawing Sheets

FOREIGN PATENT DOCUMENTS

JP          3264828 B2      3/2002

OTHER PUBLICATIONS

"Quantitative Nondestructive Evaluation", vol. 5, Jul. 31-Aug. 2005.

"Delta Technique extends the Capabilities of Wells Quality Assurance", British Journal of N.D.T., B.T. Cross et al., Dec. 1969.

"Development of a Multi-Beam Laser Ultrasonic Inspection System and Its Application on Flaw Sizing", Criepi Report, Tetsuo Fukuchi et al., Aug. 2006.

"Choonpa Tanshou-ho" Nikkan Kogyo Shinbunsha, 1974.

"Flaw Height Measuring Method by Tip Echo Techniques Standardized by The Japanese Society for Non-Destructive Inspection", The Japanese Society for Non-Destructive Inspection, Jun. 1, 1997.

"Flaw Height Measuring Method by TOFD Method Standardized by The Japanese Society for Non-Destructive Inspection", The Japanese Society for Non-Destructive Inspection, Dec. 1, 2001.

"Proposal of Simple Flaw Sizing Method in Ultrasonic Flaw Detection test", Program & Abstracts of Second Academic Lecture, The Japan Society of Maintenology, Hiroyuki Fukutomi, et al. 2005.

"SPOD-ho ni yoru kizufukasa no Sokutei—Sono 1:SPOD-ho no Teian" Dai 13 Kai Choopna ni yoru Hihakai Hyoka Symposium Koen Ronbunsha, Lin Shan et al., Jan. 24, 2006, p. 115-120.

"SPOD-ho ni yoru kizufukasa no Sokutei—Sono 1:SPOD-ho no Teian" Dai 13 Kai Choopna ni yoru Hihakai Hyoka Symposium Koen Ronbunsha, Lin Shan et al., Jan. 24, 2006, p. 121-124.

* cited by examiner

ULTRASONIC FLAW DETECTION APPARATUS AND ULTRASONIC FLAW DETECTION PROGRAM

TECHNICAL FIELD

The present invention relates to an ultrasonic flaw detection apparatus and an ultrasonic flaw detection program. More particularly, the present invention relates to an ultrasonic flaw detection apparatus and an ultrasonic flaw detection program capable of performing a plurality of ultrasonic flaw detection methods.

BACKGROUND ART

It is known in the art that a stress corrosion cracking occurs in a weld of piping of a recirculation system of a boiling light-water reactor plant. Further, existing thermal power generating facilities are toward age deteriorations; in actual fact, European countries and the United States have experienced accidents in which high temperature steam pipes of aging thermal power plants ruptured due to cracking in a heat-affected zone caused by the occurrence of creep voids and the coupling thereof. From these problems, needs for non-destructive inspection to a weld of a thick pipe such as a weld of piping of a power generation plant, in particular, needs for sizing for detecting a generating end and a terminating end of a flaw and accurately measuring a flaw height have been increased.

As ultrasonic flaw detection methods capable of measuring a flaw height, there are, for example, a normal flaw detection method of normally transmitting an ultrasonic wave onto a flaw detection surface by a normal probe and receiving the ultrasonic wave by the normal probe therefrom, an angle flaw detection method of causing an ultrasonic wave to be incident on a flaw detection surface obliquely and receiving an echo of an edge (Non-Patent Document 1), a TOFD (Time of Flight Diffraction) method by which a longitudinal wave is caused to be incident from one of a pair of angle probes disposed by facing each other and a diffracted wave generated at an edge of a flaw is received by the other of the probes (Non-Patent Document 2), and further a measurement method called an SPOD (Short Path of Diffraction) method proposed by the inventors (Non-Patent Document 3). Meanwhile, in the SPOD method, an angle probe is combined with a normal probe, an ultrasonic wave pulse is caused to be obliquely incident on a flaw detection surface, a diffracted wave generated at an edge of a flaw is received by the normal probe above the flaw, and a flaw height is determined from the difference between the arriving times of as component which directly propagates above the flaw and a component which propagates above the flaw after it is reflected on the back surface of a member to be inspected.

In addition to the ultrasonic flaw detection methods described above, there are also proposed, for example, a method for using a secondary creeping wave which is generated when an ultrasonic transverse wave is reflected on the back surface of a specimen and an ultrasonic flaw detection method using a phased array probe.

Non-Patent Document 1: The Japanese Society for Non-Destructive Inspection, "Flaw Height Measuring Method by Tip Echo Techniques Standardized by The Japanese Society for Non-Destructive Inspection", published on Jun. 1, 1997.

Non-Patent Document 2: The Japanese Society for Non-Destructive Inspection, "Flaw Height Measuring Method by TOFD Method Standardized by The Japanese Society for Non-Destructive Inspection", published on Dec. 1, 2001.

Non-Patent Document 3: FUKUTOMI Hiroyuki, LIN Shan, OGATA Takashi "Proposal of Simple Flaw Sizing Method in Ultrasonic Flaw Detection Test", Program & Abstracts of Second Academic Lecture, The Japan Society of Maintenology, 2005.

DISCLOSURE OF THE INVENTION

Problems to be Solved by the Invention

However, since the ultrasonic flaw detection methods described above have advantages and disadvantages, respectively, a more suitable ultrasonic flaw detection method must be selected according to a test environment. For example, the normal flaw detection is suitable for inspection of a steel plate or the like. However, since an ultrasonic wave is normally incident on a specimen, a problem arises in that it is difficult to detect the position of a flaw. Further, the angle flaw detection can be also used to austenitic stainless steel, Inconel (registered trademark of Special Metals Corporation) and the like. However, there is a case where weakness of an edge echo causes stress corrosion cracking to be detected in a weld of stainless steel. In such a case, abundant experiences and excellent skills are required of inspectors. Actually, however, experiences and skills of inspectors are different from one another, which sometimes results in failure of a precise measurement.

Although the TOFD method can accurately measure a flaw height, it is difficult to measure the position of a flaw by the method. Further, the TOFD method is also disadvantageous in that since a specimen whose flaw height can be accurately measured is limited to carbon steel or the like, the TOFD method cannot be used to thick structures composed of a material having a large crystal grain, for example, austenitic stainless steel, Inconel, and the like because it is difficult to detect a diffracted wave by the TOFD method.

The SPOD method is very excellent as compared with conventional ultrasonic flaw detection method because it is more excellent in a flaw detection sensitivity than the other methods because it can receive a weak diffracted wave in a shorter beam path and can be applied to thick structures of stainless steel and the like to which the TOFD method cannot be applied. Regardless of the above advantages, the SPOD method is disadvantageous in that it has a region which is difficult to be detected by the method and that it is more difficult for the SPOD method to inspect the periphery of a weld reinforcement portion of the welding than the angle flaw detection method.

From what has been described above, it is contemplated to perform a flaw detection test in combination with other measurement methods when presence or absence of a flaw and a flaw height are analyzed by the flaw detection test so that a more accurate ultrasonic flaw detection can be realized by compensating the defects of the flaw detection test and the other measurement methods.

However, to switch the plurality of ultrasonic flaw detection methods, troublesome tasks such as a change of the position where a probe is disposed, a change of a connecting mode of a flaw detector and the probe in an ultrasonic flaw detection apparatus, and the like are necessary each time the methods are switched. However, it is difficult for inspectors to perform the flaw detection test to the same specimen using the plurality of flaw detection methods. Accordingly, it is not practical to perform the flaw detection test to the same specimen using the plurality of ultrasonic flaw detection methods because inspection is time consuming as well as a switching task is difficult. Further, to realize the plurality of conventional flaw detection methods, a pulse receiver must be provided with a plurality of reception units and transmission units. The pulse receiver having the plurality of channels is ordinarily expensive and the cost of a flaw detection test is increased thereby.

Accordingly, an object of the present invention is to provide an ultrasonic flaw detection test apparatus and an ultrasonic flaw detection test program which can select an optimum ultrasonic flaw detection method according to a test environment by easily switching a plurality of ultrasonic flaw detection methods and further can measure a flaw height promptly and accurately from a result of a plurality of measured results with a smaller dispersion of inspectors.

Means for Solving the Problem

To solve the problem, an ultrasonic flaw detection apparatus according to claim 1 includes an angle probe, a normal probe, and a switching circuit for permitting connection of the angle probe and the normal probe to a transmission unit and a reception unit of a flaw detector to be optionally switched. In the ultrasonic flaw detection apparatus according to claim 1, the switching circuit can select an angle flaw detection mode for transmitting and receiving an ultrasonic beam only by the angle probe, an SPOD mode for transmitting the ultrasonic beam by the angle probe and receiving the diffracted wave propagating on a flaw detection surface above a flaw by the normal probe, a mode for simultaneously executing the angle flaw detection method and the SPOD method for transmitting the ultrasonic beam by the angle probe and receiving the reflected wave by the angle probe as well as receiving the diffracted wave propagating on the flaw detection surface above the flaw by the normal probe, and a normal flaw detection mode for transmitting and receiving the ultrasonic beam only by the normal probe.

An ultrasonic flaw detection apparatus according to claim 2 includes a first angle probe, a second angle probe disposed by facing the first angle probe, and a switching circuit for permitting connection of the respective angle probes to a transmission unit and a reception unit of a flaw detector to be optionally switched. In the ultrasonic flaw detection apparatus according to claim 2, the switching circuit can select an angle flaw detection mode for transmitting and receiving an ultrasonic beam only by the first angle probe, a TOFD mode for transmitting the ultrasonic beam by the first angle probe and receiving a surface wave and a diffracted wave by the second angle probe, a mode for simultaneously executing the angle flaw detection method and the TOFD method for transmitting the ultrasonic beam by the first angle probe and receiving the reflected wave by the first angle probe as well as receiving the surface wave and the diffracted wave by the second angle probe, and an angle flaw detection mode for transmitting and receiving the ultrasonic beam only by the second angle probe.

An ultrasonic flaw detection apparatus according to claim 3 includes a first angle probe, a normal probe, a second angle probe disposed by facing the first angle probe across the normal probe, and a switching circuit for permitting connection of the respective angle probes to a transmission unit and a reception unit of a flaw detector to be optionally switched. In the ultrasonic flaw detection apparatus according to claim 3, the switching circuit can select an angle flaw detection mode for transmitting and receiving an ultrasonic beam only by the first angle probe, an SPOD mode for transmitting the ultrasonic beam by the first angle probe and receiving the diffracted wave propagating on a flaw detection surface above a flaw by the normal prove, a mode for simultaneously executing the angle flaw detection method and the SPOD method for transmitting the ultrasonic beam by the first angle probe and receiving the reflected wave by the first normal probe as well as receiving the diffracted wave by the normal probe, a normal flaw detection mode for transmitting and receiving the ultrasonic beam only by the normal probe, a TOFD mode for transmitting the ultrasonic beam by the first angle probe and receiving the surface wave and the diffracted wave by the second angle probe, a mode for simultaneously executing the angle flaw detection method and the TOFD method for transmitting the ultrasonic beam by the first angle probe and receiving the reflected wave by the first angle probe as well as receiving the surface wave and the diffracted wave by the second angle probe, and an angle flaw detection mode for transmitting and receiving an ultrasonic beam only by the second angle probe.

Further, it is preferable that the ultrasonic flaw detection apparatus of the present invention have a peak time estimation means for estimating the time at which the peak of an echo appears from the parameters of a specimen previously set according to a flaw detection mode selected by a switching circuit and a guide display means for displaying the position of appearance of the peak of the echo estimated by the peak time estimation means to the time-axis of a display unit for displaying a detected echo by a cursor.

It is further preferable that the ultrasonic flaw detection apparatus of the present invention have an enlarged waveform display means for displaying the region of a previously designated range to a display unit in enlargement with the displayed position of the cursor located at the center of the region.

It is further preferable that a guide display means of the ultrasonic flaw detection apparatus of the present invention changes the color of a line of a waveform of a display unit or the background color of the waveform to each flaw detection mode.

It is further preferable that a guide display means of the ultrasonic flaw detection apparatus of the present invention causes a display unit to simultaneously display the waveforms formed by the plurality of ultrasonic flaw detection methods when an ultrasonic flaw detection test is executed to the specimens by the plurality of ultrasonic flaw detection methods.

An ultrasonic flaw detection program according to claim 8 causes a computer, which controls a switching circuit for arbitrarily switching connection of an angle probe and a normal probe to a transmission unit and a reception unit of a pulse receiver, to execute a circuit selection process for controlling switching of the switching circuit according to a flaw detection mode selected, by an input unit, from an angle flaw detection mode for transmitting and receiving an ultrasonic beam only by the angle probe, an SPOD mode for transmitting the ultrasonic beam by the angle probe and receiving the diffracted wave propagating on a flaw detection surface above a flaw by the normal probe, a mode for simultaneously executing the angle flaw detection method and the SPOD method for transmitting the ultrasonic beam by the angle probe and receiving the reflected wave by the angle probe as well as receiving the diffracted wave propagating on the flaw detection surface above the flaw by the normal probe, and a normal flaw detection mode for transmitting and receiving the ultrasonic beam only by the normal probe.

An ultrasonic flaw detection program according to claim 9 causes a computer, which controls a switching circuit for arbitrarily switching connection of a first angle probe and a second angle probe disposed by facing the first angle probe to a transmission unit and a reception unit of a pulse receiver, to execute a circuit selection process for controlling switching of the switching circuit according to a flaw detection mode selected, by an input unit, from an angle flaw detection mode for transmitting and receiving an ultrasonic beam only by the first angle probe, a TOFD mode for transmitting the ultrasonic beam by the first angle probe and receiving the surface wave and the diffracted wave by the second angle probe, a mode for simultaneously executing the angle flaw detection method and the TOFD method for transmitting the ultrasonic beam by the first angle probe and receiving the reflected wave by the first angle probe as well as receiving the surface wave and the diffracted wave by the second angle probe, and an angle flaw detection mode for transmitting and receiving the ultrasonic beam only by the second angle probe.

An ultrasonic flaw detection program according to claim 10 causes a computer, which controls a switching circuit for arbitrarily switching connection of a first angle probe, a normal probe, and a second angle probe disposed by facing the first angle probe to a transmission unit and a reception unit of a pulse receiver, to execute a circuit selection process for controlling switching of the switching circuit according to a flaw detection mode selected, by an input unit, from an angle flaw detection mode for transmitting and receiving an ultrasonic beam only by the angle probe, an SPOD mode for transmitting the ultrasonic beam by the first angle probe and receiving the diffracted wave propagating on a flaw detection surface above a flaw by the normal probe, a mode for simultaneously executing the angle flaw detection method and the SPOD method for transmitting the ultrasonic beam by the first angle probe and receiving the reflected wave by the first angle probe as well as receiving the diffracted wave by the normal probe, a normal flaw detection mode for transmitting and receiving the ultrasonic beam only by the normal probe, a TOFD mode for transmitting the ultrasonic beam by the first angle probe and receiving the surface wave and the diffracted wave by the second angle probe, a mode for simultaneously executing the angle flaw detection method and the TOFD method for transmitting the ultrasonic beam by the first angle probe and receiving the reflected wave by the first angle probe as well as receiving the surface wave and the diffracted wave by the second angle probe, and an angle flaw detection mode for transmitting and receiving the ultrasonic beam only by the second angle probe.

In the ultrasonic flaw detection program according to the present invention, a memory unit previously stores parameters of respective selected flaw detection modes, which are necessary to estimate the time of appearance of the peak of an echo detected in a selected flaw detection mode, and a computer is caused to execute a peak time estimation process for causing an arithmetic operation unit to calculate the time of appearance of the peak of an echo using the parameters from the memory unit as input values and a guide display process for displaying a cursor, which shows the position of appearance of the peak of the echo estimated by the peak time estimation process, to the time-axis of the detected echo displayed on a display unit.

Effect of the Invention

According to the ultrasonic flaw detection apparatus and the ultrasonic flaw detection program of the present invention, it is possible to select an optimum ultrasonic flaw detection method from a plurality of ultrasonic flaw detection methods according to a test environment only by switching operation of the switching circuit. Moreover, an inspector can execute the plurality of flaw detection methods continuously or simultaneously as necessary only by a simple switching operation of the flaw detection mode switches so that an inspection time can be reduced. Further, since the plurality of ultrasonic flaw detection tests can be easily executed to the same specimen, the defects of the ultrasonic flaw detection methods can be covered as well as a synergetic effect can be expected. As a result, a more accurate flaw detection test can be promptly executed. The following patterns of flaw detection methods can be selectively executed. For example, according to the invention of claim 1, the four patterns of the flaw detection modes using the angle flaw detection method, the SPOD method, the combination of the angle flaw detection method and the SPOD method, and the normal flaw detection method can be selectively executed. According to the ultrasonic flaw detection apparatus of claim 2, the four patterns of the flaw detection modes using the angle flaw detection method from different directions, the TOFD method, and the combination of the angle flaw detection method and the TOFD method can be selectively executed. Further, according to the ultrasonic flaw detection apparatus of claim 3, the seven patterns of the flaw detection modes using the angle flaw detection method from different directions, the SPOD method, the combination of the SPOD method and the angle flaw detection method, the normal flaw detection method, the TOFD method, and the combination of the TOFD method and the angle flaw detection method can be selectively executed. Accordingly, it is possible to select a flaw detection method most suitable for the test environment can be selected and easily executed in combination with the plurality of flaw detection methods. As a result, since measurement can be executed making use of the advantages of the respective methods, a more accurate ultrasonic flaw detection test can be executed.

Further, it is sufficient for the flaw detector to have at least each one set of the transmission unit and the reception unit required thereto, and each one set of the transmission unit and the reception unit can receive all the flaw detection modes. Accordingly, since it is not necessary to provide a plurality of reception units, a pulse receiver having a minimum performance of one channel for reception can be used. Thus, the cost of the pulse receiver can be reduced as well as the cost of the flaw detection test can be reduced.

Further, according to the ultrasonic flaw detection apparatus of claim 4, since necessary parameters are previously set according to a selected flaw detection mode, the time at which the peak of an echo appears and which is used as a reference of a waveform analysis can be calculated in the respective ultrasonic flaw detection methods and a cursor showing the time of appearance of the estimated peak of an echo can be displayed to the time-axis of a display unit. Since the inspector can previously find the position at which a waveform to be noted appears in each flaw detection method, he or she can very easily observe a waveform by observing it at a central portion of the displayed cursor.

Further, according to the ultrasonic flaw detection apparatus of claim 7, since a predetermined region including the cursor portion at the center thereof is displayed in enlargement, the inspector can easily confirm whether or not a flaw is present and a target echo by observing the waveform in the portion displayed in enlargement.

Further, according to the ultrasonic flaw detection apparatus of claim 8, since the inspector can recognize that from which flaw detection method a waveform is obtained from the difference of a background color, the inspector is less likely to take a flaw detection method being executed by mistake.

Further, according to the ultrasonic flaw detection apparatus of claim 9, since the inspector can observe the waveforms obtained by the plurality of ultrasonic flaw detection methods on one screen at the same time, a more accurate ultrasonic flaw detection can be realized by complementing the information, which cannot be obtained by executing only one flaw detection method, by the information obtained from another flaw detection method.

BRIEF DESCRIPTION OF THE DRAWINGS

FIG. 5A shows the peak time of an echo measured by an angle flaw detection. FIG. 5B shows the peak time of an echo measured by an SPOD method. FIG. 5C shows the peak time of an echo measured by a normal flaw detection.

FIG. 10A shows a waveform measured by the angle flaw detection. FIG. 10B shows a waveform measured by the SPOD method. FIG. 10C shows a waveform measured by the angle flaw detection method and the SPOD method. FIG. 10D shows a waveform measured by a normal flaw detection.

FIG. 12A shows the peak time of an echo measured by the angle flaw detection. FIG. 12B shows the peak time of an echo measured by a TOFD method.

EXPLANATION OF REFERENCE NUMERALS

Figure 1:
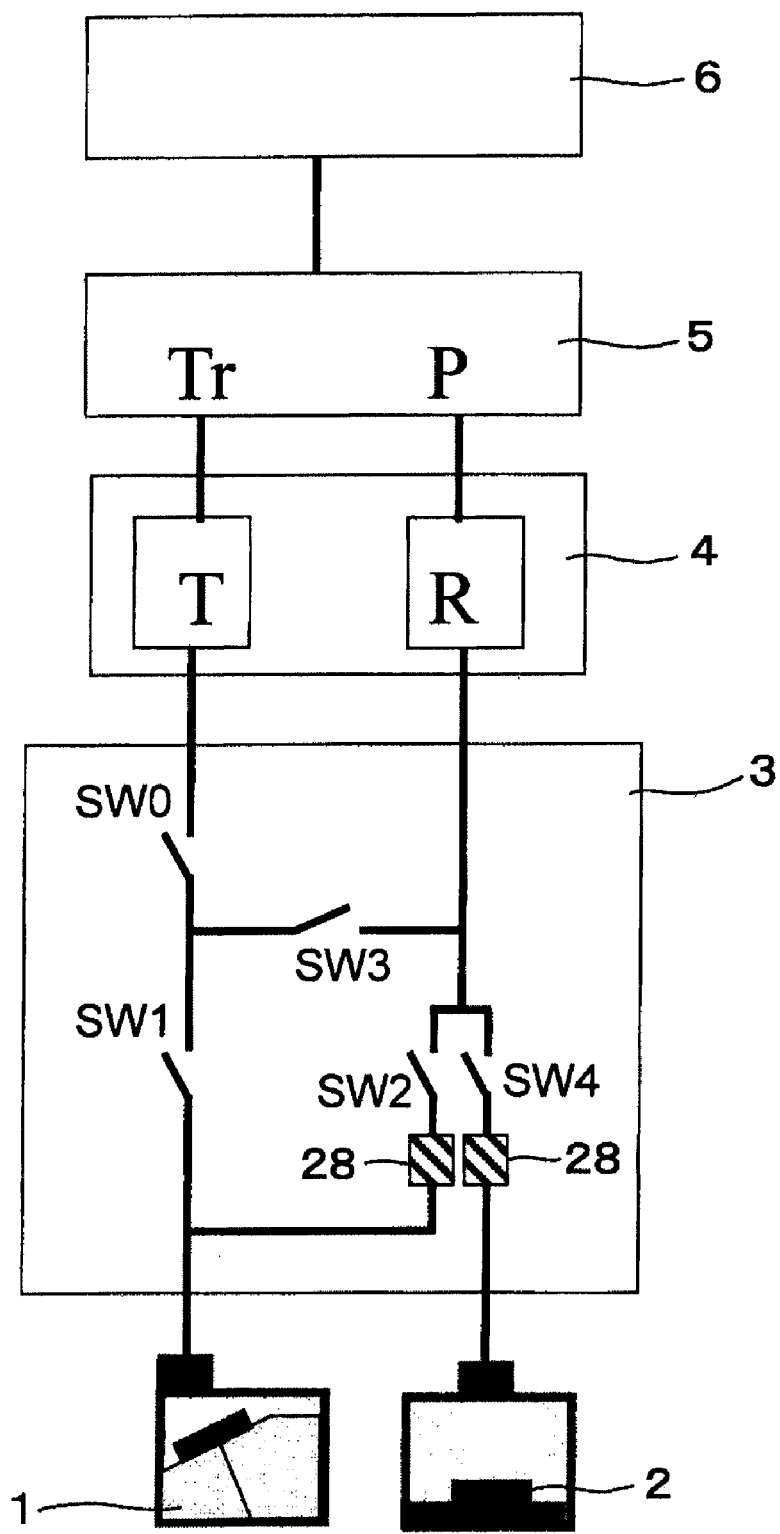
FIG. 1 is a block diagram showing an example of an ultrasonic flaw detection apparatus according to a first embodiment.

1 Angle probe (first angle probe)
2 Normal probe
29 Angle probe (second angle probe)
3 Switching circuit
4 Pulse receiver
5 A/D conversion board
6 Personal computer
7 Display device
14 Circuit selection means
15 Peak time estimation means
16 Guide display means
17 Enlarged waveform display means
26 Specimen
27 Cursor

BEST MODE FOR CARRYING OUT THE INVENTION

An arrangement of the present invention will be described below in detail based on a best mode shown in the drawings.

FIGS. 1 to 10 show a first embodiment of the present invention. In an ultrasonic flaw detection apparatus of the first embodiment, a personal computer 6, which collects data and acts as a controller, is used, and it is configured so as to control an angle probe 1 and a normal probe 2 through a pulse receiver 4 and a switching circuit 3 connected through an A/D conversion board 5. The angle probe 1 and the normal probe 2 are connected to a transmission unit T and a reception unit R of the pulse receiver 4 through the switching circuit 3 so that they can be optionally switched. Meanwhile, the angle probe 1 and the normal probe 2 can transmit and receive an ultrasonic beam, respectively, and act as a transmission probe or a reception probe depending on a mode selected by the switching circuit 3.

Figure 2:
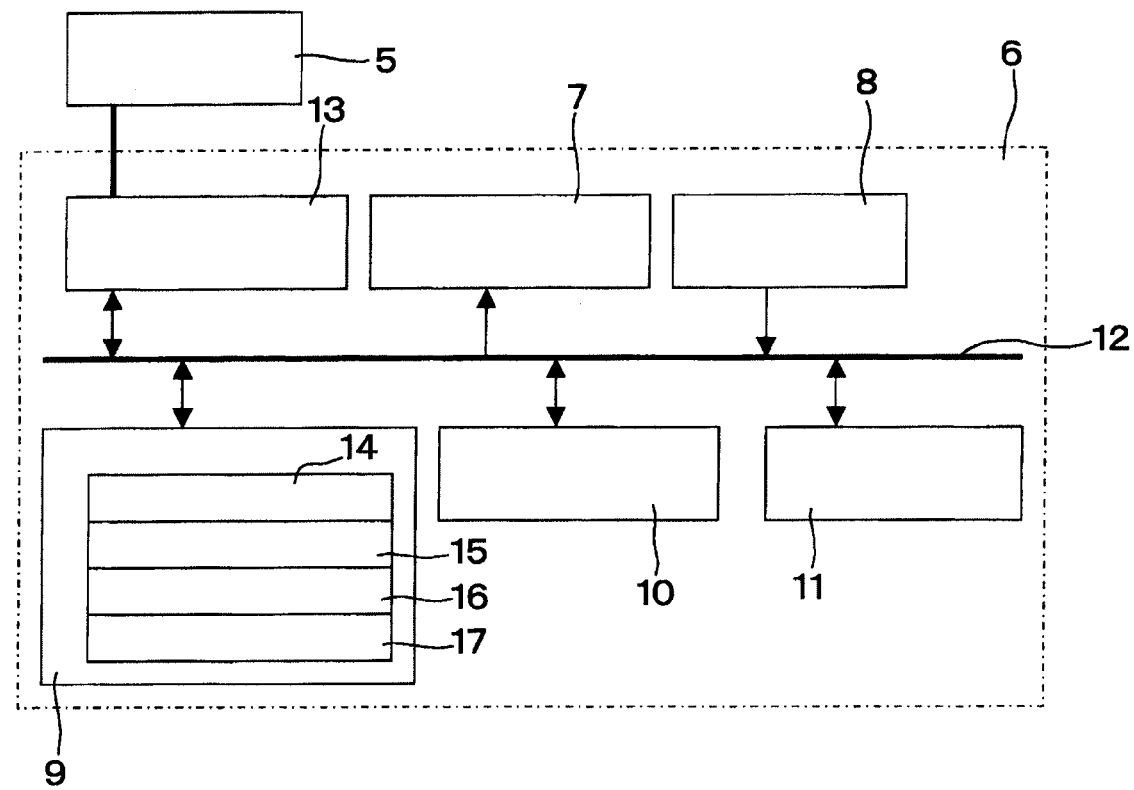
FIG. 2 is a block diagram showing an example of a computer according to the first embodiment.

As shown in FIG. 2, the personal computer 6 has a display unit 7, an input unit 8 such as a keyboard, a mouse, and the like, an arithmetic operation unit (CPU) 9, a main memory (RAM) 10, and an auxiliary memory 11 such as a hard disc and the like so as to constitute a function corresponding to a flaw detector. Note that the main memory 10 and the auxiliary memory 11 are simply called a memory generically. Further, the computer 6 realizes a circuit selection means 14, a peak time estimation means 15, a guide display means 16, and an enlarged waveform display means 17 on the computer by executing a program stored in the auxiliary memory 11. In the computer 6, the circuit selection means 14 executes a circuit selection process for controlling switching the switches SW0 to SW4 by issuing a signal for changing the connection arrangement of the switches to the switching circuit 3 which selects the transmission probe and the reception probe according to a flaw detection mode selected from the input unit 8; the peak time estimation means 15 executes a peak time estimation process for previously storing parameters necessary to calculate the time of appearance of an echo to be noted in a flaw detection mode selected in the circuit selection means 14 and causing the arithmetic operation unit 9 to calculate the time at which the peak of the echo appears using the stored parameters as input values; the guide display means 16 executes a guide display process for causing the time-axis of the detected echo displayed in the display unit 7 to display the cursor 27 showing the position of appearance of the peak of the echo estimated by the peak time estimation means 15; and the enlarged waveform display means 17 executes an enlarged waveform display process for displaying the region of a previously designated range in enlargement with the display position of the cursor 27 displayed by the guide display means 16 located at the center of the region. The above hardware resources are electrically connected through, for example, a bus 12 and connected to the A/D conversion board 5 through an input/output I/F 13.

In the embodiment, although the function corresponding to the flaw detector is composed of the computer 6, the A/D conversion board 5, and the pulse receiver 4, the computer 6 may be used only to collect data using an independent flaw detector. The pulse receiver 4 drives the transmission probe and the reception probe based on a command from the CPU 9 of the computer 6 or by directly controlling the pulse receiver 4. In the display unit 7, the time, which is necessary for a pulse reflection wave to return, is shown on the lateral axis, and the intensity of an ultrasonic wave, i.e., the height of an echo, which is reflected and returned, is shown on the vertical axis; hereinafter, it is simply called a waveform.

Figure 3:
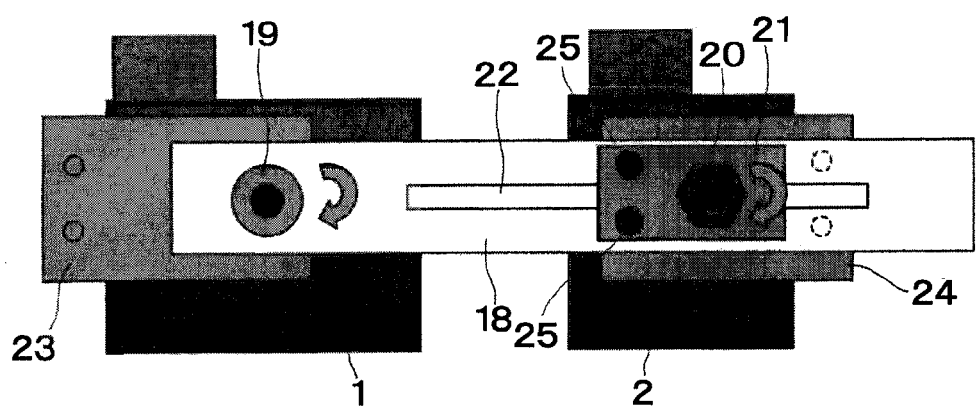
FIG. 3 is a plan view showing a probe holder.
Figure 4:
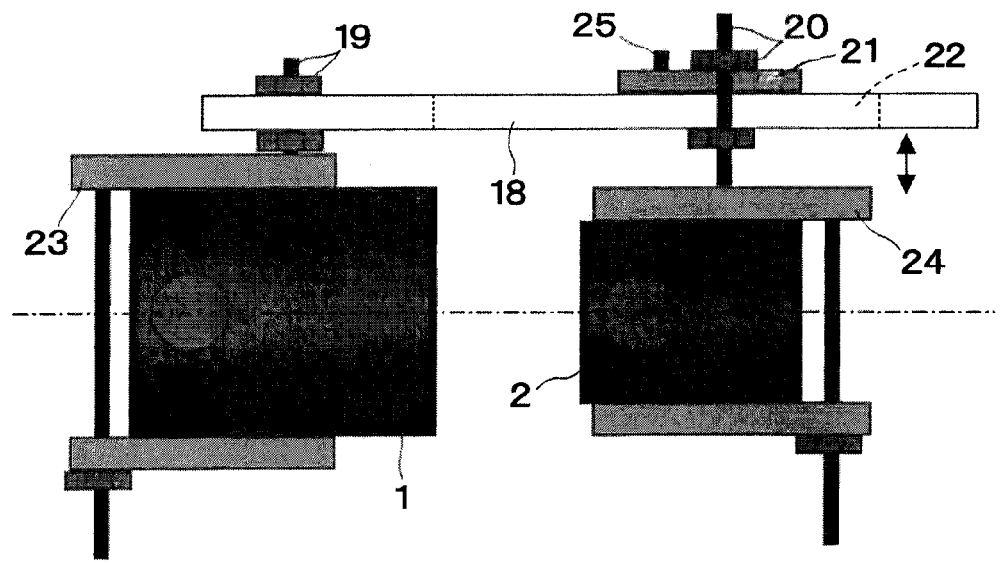
FIG. 4 is a side elevational view of the probe holder.

In the embodiment, as shown in FIGS. 3 and 4, the angle probe 1 and the normal probe 2 are coupled with each other by a plate-shaped coupling member 18 and are arranged to move the same distance in the same direction at the same time while keeping a predetermined gap therebetween. When an SPOD method is executed, an echo, which directly propagates above a flaw of a diffracted wave, and an echo, which propagates above the flaw after it is reflected on a back surface once, appear simultaneously at the same difference in arrival times without fail regardless of the intensity of a signal. As a result, the position of a flaw height or the height of a flaw itself can be simply found by coupling the probe 1 for transmission with the probe 2 for reception by the coupling member 18 and moving them while keeping a predetermined interval therebetween. It is preferable here that the interval between the angle probe 1 and the normal probe 2 be adjusted by arranging the coupling member 18 so as to make the attachment position thereof to at least one of the probes changeable. For this purpose, the coupling member 18 has a slot 22 formed in a longitudinal direction and can adjust the interval between the angle probe 1 and the normal probe 2 by linearly movably fixing any one of the probes 1, 2 coupled with each other making use of the slot 22. That is, one of the probes, for example, the angle probe 1 is fixed to one end of the coupling member 18 by a clamp screw 19 so that the angle thereof can be adjusted, whereas the other probe, for example, the normal probe 2 is attached to the coupling member 18 through a clamp screw 20 passing through the slot 22 and a stopper 21 so that the angle of the normal probe 2 can be adjusted. The angle probe 1 is held by the coupling member 18 by fixing the clamp screw 19 to a jig 23, which clamps both sides of the angle probe 1, by welding, adhesive, and the like. Similarly, the normal probe 2 is also held by the coupling member 18 by fixing a clamp screw 20 to a jig 24, which clamps both the sides of the normal probe 2 by welding, adhesion, and the like. Further, the normal probe 2 is positioned relative to the coupling member 18 by fixing the clamp screw 20 to the stopper 21 and fixing the stopper 21 to the coupling member 18. A screw 25 is disposed to the stopper 21, and the stopper 21 is integrated with the coupling member 18 by friction caused by tightening of the screw 25 so that the position of the normal probe 2 can be fixed. Accordingly, the position at which the normal probe 2 is fixed is moved within the range of the slot 22 by loosening the clamp screw 20 so that the interval between the angle probe 1 and the normal probe 2 can be adjusted.

Further, although it is preferable to use a longitudinal wave as the ultrasonic beam, the ultrasonic beam is not limited to the longitudinal wave, and a transverse wave may also be used. A reason why the longitudinal wave is used lies in that it is unlikely to be affected by a metal structure because of its long wavelength in addition to that it reaches a probe sooner than the transverse wave. However, since the transverse wave can be also received, the longitudinal wave can be complemented by the transverse wave when the longitudinal wave cannot be received for any reason.

The transmission probe and the reception probe can also measure a flaw by executing scanning independently. For example, a flaw can be also detected by moving the transmission probe while fixing the reception probe above the flaw or by moving the reception probe while fixing the transmission probe above the flaw inversely.

The switching circuit 3 can control a plurality of switches based on a command from the CPU 9 of the computer or by directly controlling the pulse receiver 4 so that the switches are electrically turned on and off.

Specifically, the switching circuit 3 of the embodiment is arranged such that connection of any one or both of the angle probe 1 and the normal probe 2 to the transmission unit and the reception unit of the pulse receiver 4, which constitutes the flaw detector, is optionally switched by combining five switches SW0 to SW4 which can be electrically turned on and off so that the four flaw detection modes described below can be selectively performed. That is, switches SW0 and SW1 are inserted between the transmission unit T of the pulse receiver 4 and the angle probe 1 in series, the switch SW4 is inserted between the reception unit R and the normal probe 2 in series as well as the switch SW2 which connects the reception unit R and the angle probe 1 is disposed side by side with the switch SW4, and further the switch SW3 is disposed to connect the upstream side of the switch SW1 and the upstream sides of the switches SW4 and SW2. Here, the switch SW0 is a main power supply switch which is turned on when a flaw detection test is started and is turned off after the test is finished. Further, reference numeral 28 denotes a variable amplifier which can amplify a weak diffracted wave when necessary.

(1) First Mode

Figure 5A:
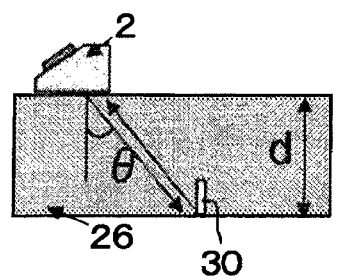
FIGS. 5A to 5C are explanatory views showing the peak times of echoes.

When the switches SW1 and SW2 are turned on and the switches SW3 and SW4 are turned off, only the angle probe 1 is connected to the transmission unit T and the reception unit R of the pulse receiver 4, and only the angle probe 1 transmits and receives an ultrasonic beam, thereby a so-called angle flaw detection mode for receiving an edge echo from a flaw 30 is executed as shown in FIG. 5A.

(2) Second Mode

Figure 5B:
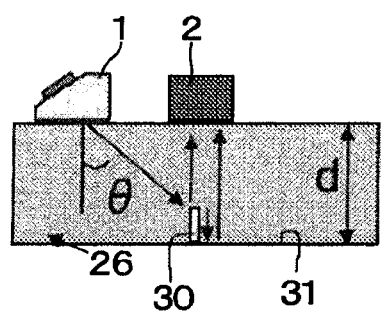

When the switches SW1 and SW4 are turned on and the switches SW2 and SW3 are turned off, the angle probe 1 is connected to the transmission unit T of the pulse receiver 4 and the normal probe 2 is connected to the reception unit R of the pulse receiver 4, respectively. With this, as shown in FIG. 5B, a so-called SPOD mode is executed in which the normal probe 2 receives a diffracted wave 32, which is generated at a tip of a flaw 30 by an ultrasonic wave incident from the angle probe 1 and directly propagates above the flaw 30, and a diffracted wave 33, which propagates above the flaw 30 after it is once reflected on a back surface 31.

(3) Third Mode

When the switches SW1, SW2, and SW4 are turned on and the switch SW3 is turned off, the angle probe 1 is connected to the transmission unit T and to the reception unit R and the normal probe 2 is connected to the reception unit R, respectively at the same time. As a result, a so-called angle flaw detection method and an SPOD method are executed at the same time in which the angle probe 1 causes an ultrasonic wave to be incident and receives an tip echo, and, at the same time, the normal probe 2 receives a diffracted wave 32, which is generated at a tip of a flaw 30 and directly propagates above the flaw 30, and a diffracted wave 33, which propagates above the flaw after it is once reflected on a back surface 31.

(4) Fourth Mode

Figure 5C:
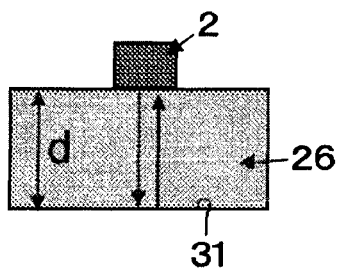

When the switches SW3 and SW4 are turned on and the switches SW1 and SW2 are turned off, a so-called normal flaw detection mode is executed in which only the normal probe 2 is connected to the transmission unit T and the reception unit R of the pulse receiver 4 and only the normal probe 2 causes an ultrasonic wave to be incident and receives an edge echo as shown in FIG. 5C.

Further, when a waveform is displayed on the display unit 7, it may be displayed likewise an ordinary flaw detector. However, it is preferable that the display unit 7 has a waveform display function for estimating the time, at which the peak of a detected echo, which is different in each flaw detection mode, appears and previously displaying the position, at which the peak of the detected echo appears, on the time-axis of the display unit by a cursor. In the display unit 7, the lateral axis shows the time which is necessary for a reflected pulse wave to return, and the vertical axis shows the intensity, i.e., the height of echo, of the ultrasonic wave which is reflected and returned. In the embodiment, the time-axis of a waveform, i.e., the lateral axis, is synchronized with the switching of the switching circuit by a trigger signal of the pulse receiver 4 for exciting the probe.

When a parameter for prescribing a beam path is previously determined or assumed in a material in which it is contemplated that an ultrasonic wave has substantially a fixed speed, a propagation time, that is, the arrival time of an echo can be determined by calculation. Thus, to calculate and estimate the time at which an echo to be noted, i.e., a position at which the height of the echo is maximized, appears in each flaw detection test, parameters, which are necessary to estimate the time at which an echo wave is received, such as the thickness of a specimen, the speed of an ultrasonic wave that propagates in the specimen, the delay time in an angle wedge, the angle of incidence of the ultrasonic wave, the estimated height of a flaw, and the like must be selected and previously set for each flaw detection test method.

Figure 6:
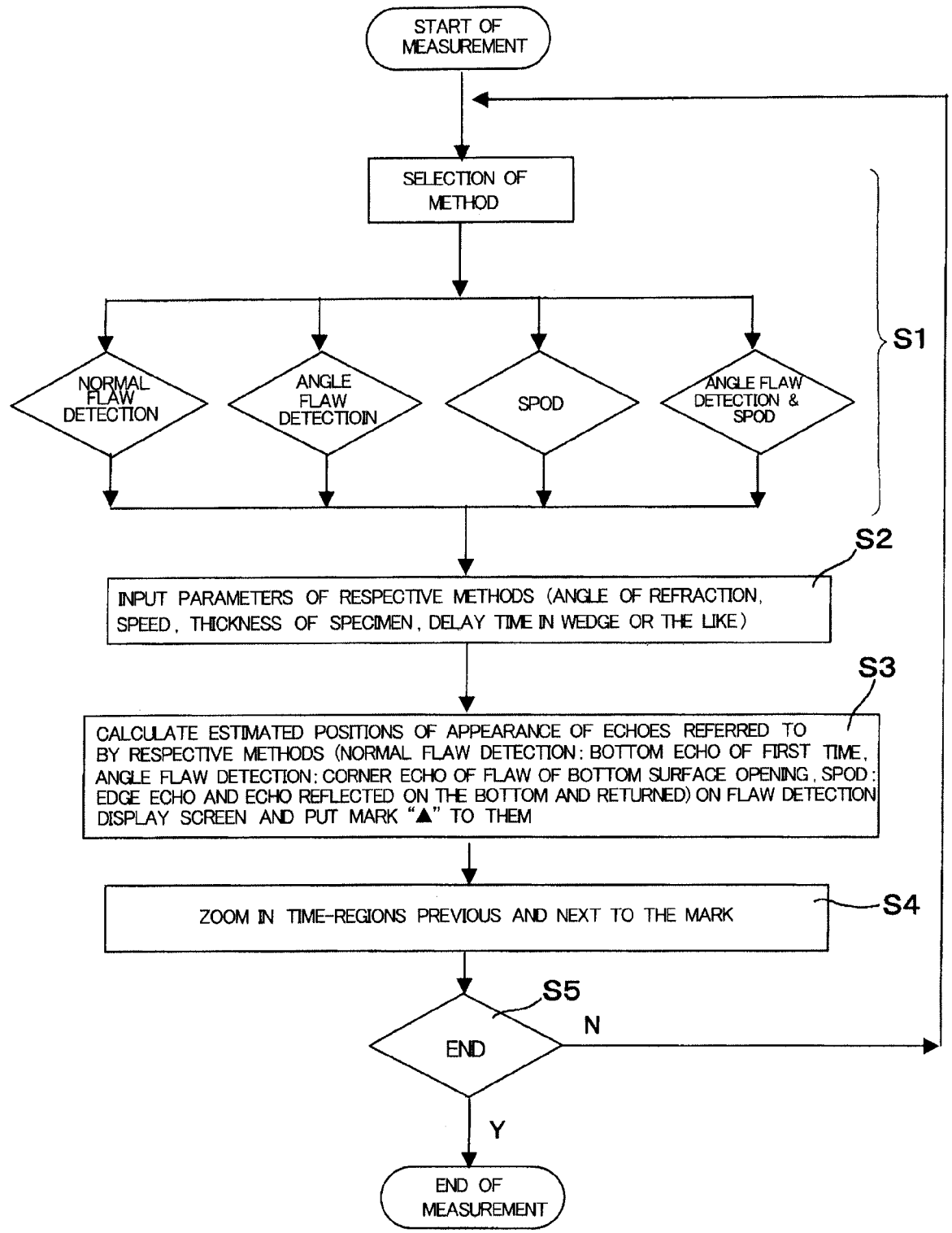
FIG. 6 is a flowchart showing an example of a process executed by an ultrasonic flaw detection program of the present invention.

The selection of the flaw detection modes described above and the estimation and the display of the position of appearance of the peak of an echo detected in each flaw detection mode can be realized by executing an ultrasonic flaw detection program by a computer which is to be described below. FIG. 6 shows a flow of a process executed by the ultrasonic flaw detection program of the embodiment. In the ultrasonic flaw detection apparatus of the embodiment, first, an ultrasonic flaw detection method to be executed is selected (S1), and then parameters, which are necessary to the selected flaw detection mode, are input or selected from a database (S2). The time of appearance of an echo in the selected ultrasonic flaw detection method is calculated and shown on the display unit 7 by the cursor 27 (S3). Next, an image is shown in enlargement with the cursor 27 showing the estimated position of appearance of the echo located at the center of the image (S4), and the flow is finished by finally determining the end of the flow (S5).

First, an ultrasonic flaw detection method to be executed when a process is started is selected (S1). In the embodiment, for example, selection buttons are displayed on the display unit 7, and the method is selected by selecting the selection buttons by the input unit 8 such as the mouse and the like. Although the selection buttons have marks such as "normal flaw detection", "angle flaw detection", "SPOD method", and "angle flaw detection & SPOD method" displayed thereon, the marks are not limited thereto. When any of the ultrasonic flaw detection methods is selected, the circuit selection means 14 executes the switching control of the switching circuit 3 according to a selected ultrasonic flaw detection method. The switching control of the switching circuit may be performed using a known technology, and the method of performing it is not particularly limited. Further, the respective switches may be manually turned on and off depending on a case. The information showing any of the flaw detection methods is selected is stored in, for example, the main memory 10 as a parameter and referred to until the process is finished.

Next, parameters are set (S2). The embodiment employs (1) the thickness of a specimen, (2) the speed of an ultrasonic wave propagating in the specimen, (3) the delay time in angle wedge, (4) the angle of incidence of an ultrasonic beam, and (5) the estimated height of a flaw as parameters according to the four flaw detection modes. Here, it is not necessary to input all the parameters in all the flaw detection methods, and it is sufficient to appropriately input necessary parameters according to a selected flaw detection method. These parameters are, for example, stored in the main memory 10 by displaying a parameter input screen on the display unit 7 and inputting them by the inspector.

For example, the parameters are determined as described below.

(1) The thickness d of the specimen can be measured by a thickness gauge.

(2) The speed c of the ultrasonic wave in the specimen is uniquely determined from the material of the specimen 26.

Figure 7:
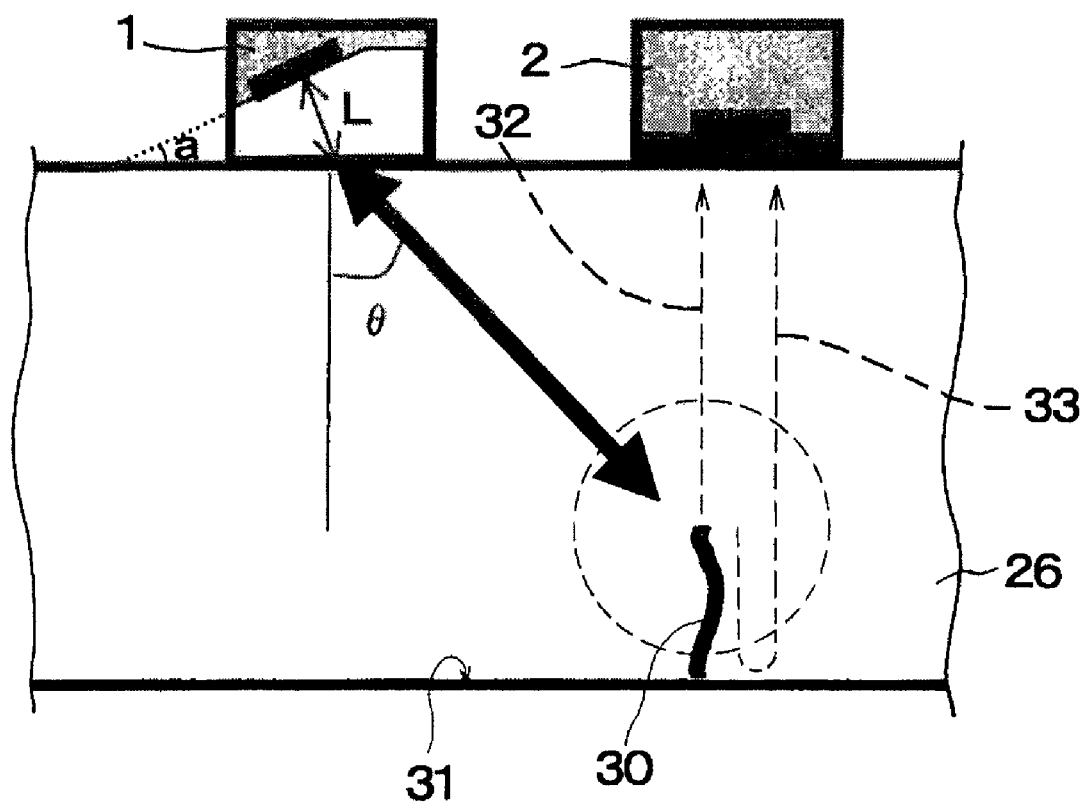
FIG. 7 is a view showing an example of a delay time in an angle wedge and a refractive angle of an ultrasonic beam.

(3) The delay time $t_d$ in the angle wedge is a parameter which is necessary in the angle flaw detection and the SPOD method and can be determined by Expression 1 in, for example, a case shown in FIG. 7.

$$t_d = L/C_1 \qquad \text{<Expression 1>}$$

Here, L shows the propagation distance of the ultrasonic wave in the wedge, and $C_1$ shows the speed of a longitudinal wave in the wedge.

(4) The angle of incidence θ is a parameter which is necessary in the angle flaw detection and the SPOD method. For example, the angle of incidence θ can be determined from an inclining angle shown by a symbol "a" in FIG. 7 and the material of the angle wedge.

(5) The estimated height of a flaw "h" is a parameter which is necessary in the SPOD method and previously estimated. For example, since the height of a flaw is ordinarily 2 to 3 mm, the values may be input. Also, the height of a flaw may be set to a predetermined ratio (for example, 10 to 20%) to the thickness of the specimen 26. Further, when the height of a flaw was already measured by another flaw detection method, the measured value may be input. As a result, it is possible to perform a more accurate ultrasonic flaw detection test by the SPOD method based on the values measured by the normal flaw detection method and the angle flaw detection method.

Note that since these parameters are only examples, the parameters are not limited thereto. Further, the examples of parameters, which are set to, for example, each material, and target product, may be previously arranged as a database and stored in the auxiliary memory 11 and the like so that it can be omitted to set parameters each time.

Next, a guide display process will be executed. In the ultrasonic flaw detection test, an echo to be noted, i.e., position at which the height of the echo is maximized, exists in each of the flaw detection methods to be executed, and the inspector measures the height of a flaw or the like from the time of appearance of the echo. In the ultrasonic flaw detection apparatus of the present invention, the time of appearance of an echo to be noted is estimated in each flaw detection method, and the cursor 27, which indicates the time of appearance, is shown to the time-axis of a waveform so that a waveform analyzing operation performed by the inspector is supported.

Figure 8:
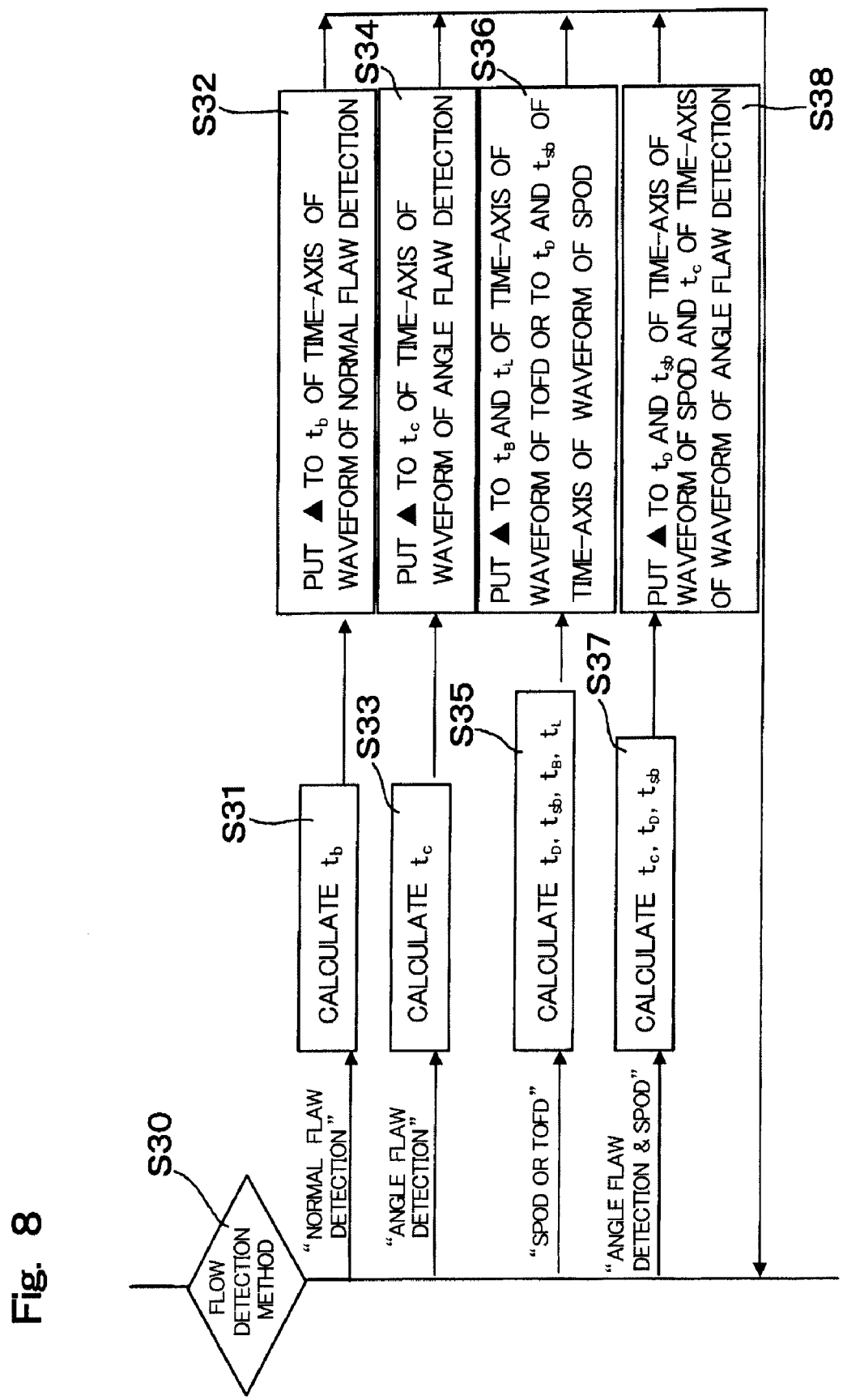
FIG. 8 is a flowchart showing an example of a guide display process.

FIG. 8 shows a detailed flowchart of the guide display process in the embodiment. First, which of the flaw detection methods is selected is determined (S30). Next, the times, i.e., the times of peak, at which the echoes of respective waveforms are maximized are calculated from the input parameters (S31, S33, S35, and S37). Here, the times of peak of the echoes of the respective waveforms mean a bottom echo in the normal flaw detection, a corner echo of a flaw in an opening of a bottom in the angle flaw detection, and an edge echo and an echo reflected on the bottom thereof in the SPOD method.

The time of appearance $t_b$ of the bottom echo in the normal flaw detection method is determined by Expression 6 (refer to FIG. 5C).

$$t_b = 2d/c \qquad \text{<Expression 2>}$$

The time of appearance to of the corner echo of the flaw in the opening of the bottom in the angle flaw detection method is determined by Expression 3 (refer to FIG. 5A).

$$t_c = 2d/(c \cos \theta) + 2t_d \qquad \text{<Expression 3>}$$

The time of appearance $t_D$ of a diffracted wave echo, which directly propagates from the flaw tip to a flaw detection surface in the SPOD method, is determined by Expression 4. Further, the time of appearance $t_{sb}$ of a bottom diffracted wave echo, which propagates to the flaw detection surface after it is once reflected on the bottom, is determined by Expression 5 (refer to FIG. 5B).

$$t_D = (d-h)/(c \cos \theta) + (d-h)/c_L + t_d \qquad \text{[Expression 4]}$$

$$t_{sb} = (d-h)/(c \cos \theta) + (d+h)/c_L + t_d = t_D + 2h/c_L \qquad \text{[Expression 5]}$$

where $c_L$ shows the speed of a longitudinal wave.

Figure 10A:
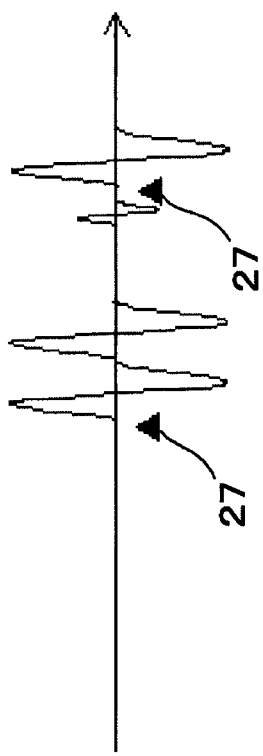
FIGS. 10A to 10D are image views showing examples of cursors displayed by the guide display process.
Figure 10C:
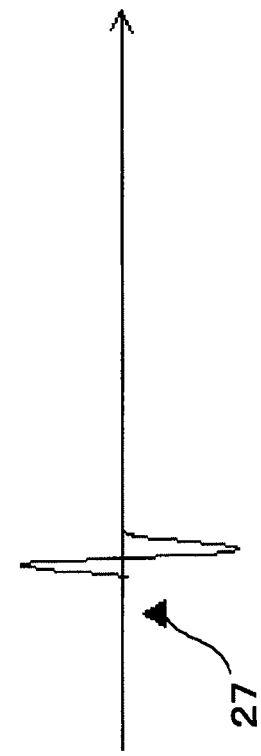
Figure 10B:
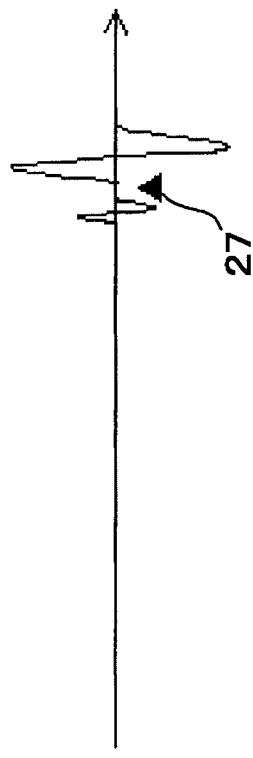
Figure 10D:
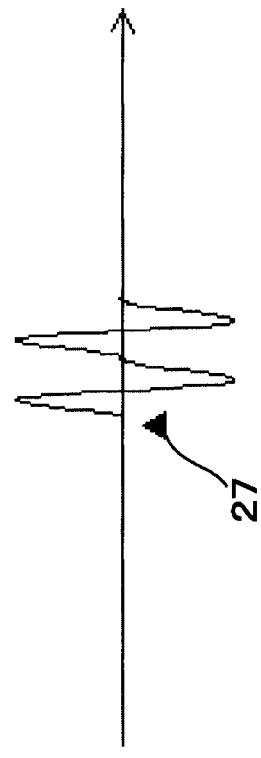

After the time of appearance of an echo in a selected flaw detection method is calculated by the above process, a process for displaying the cursor 27, for example, a figure "▲" to the position of a coordinate, to which a waveform displayed along the time-axis of the display unit 7 corresponds, is performed (S32, S34, S36, S38). FIGS. 10A to 10D show examples in which the positions, at which the peaks of detected echoes are caused to appear by the guide display process, in the respective flaw detection modes: FIG. 10A shows the time of appearance of a corner echo of a flaw in an opening of a bottom in the angle flaw detection method; FIG. 10B shows the time of appearance of an edge echo in the SPOD method; FIG. 10C shows the time of appearance of a corner echo and an edge echo of a flaw in an opening of a bottom in the angle flaw detection method and the SPOD method, and FIG. 10D shows the time of appearance of a bottom echo in the normal flaw detection method, respectively.

The screen displayed on the display unit 7 may be separated into four portions so that the waveforms of echoes in the ultrasonic flaw detections performed by the first to fourth modes can be displayed on one screen. Specifically, a plurality of waveforms can be displayed on the screen at the same time by storing the waveforms when echoes are received by the respective flaw detection methods and continuously displaying them thereon as they are. Accordingly, the inspector can measures the size, height and the like of a flaw by simultaneously observing the results obtained by the four flaw detection methods at the maximum. In doing this, screen need not be divided into the four portions and may be divided into two or three portions, and flaw detection methods to be displayed may be selected.

Further, it is preferable to change the respective waveforms to be displayed and the background colors thereof in the respective flaw detection methods. For example, the same background color may be used and waveforms may be displayed by lines having a different color. Further, in the embodiment, a flaw detection method is displayed as a title of a waveform so that the inspector does not take data by mistake.

Figure 9:
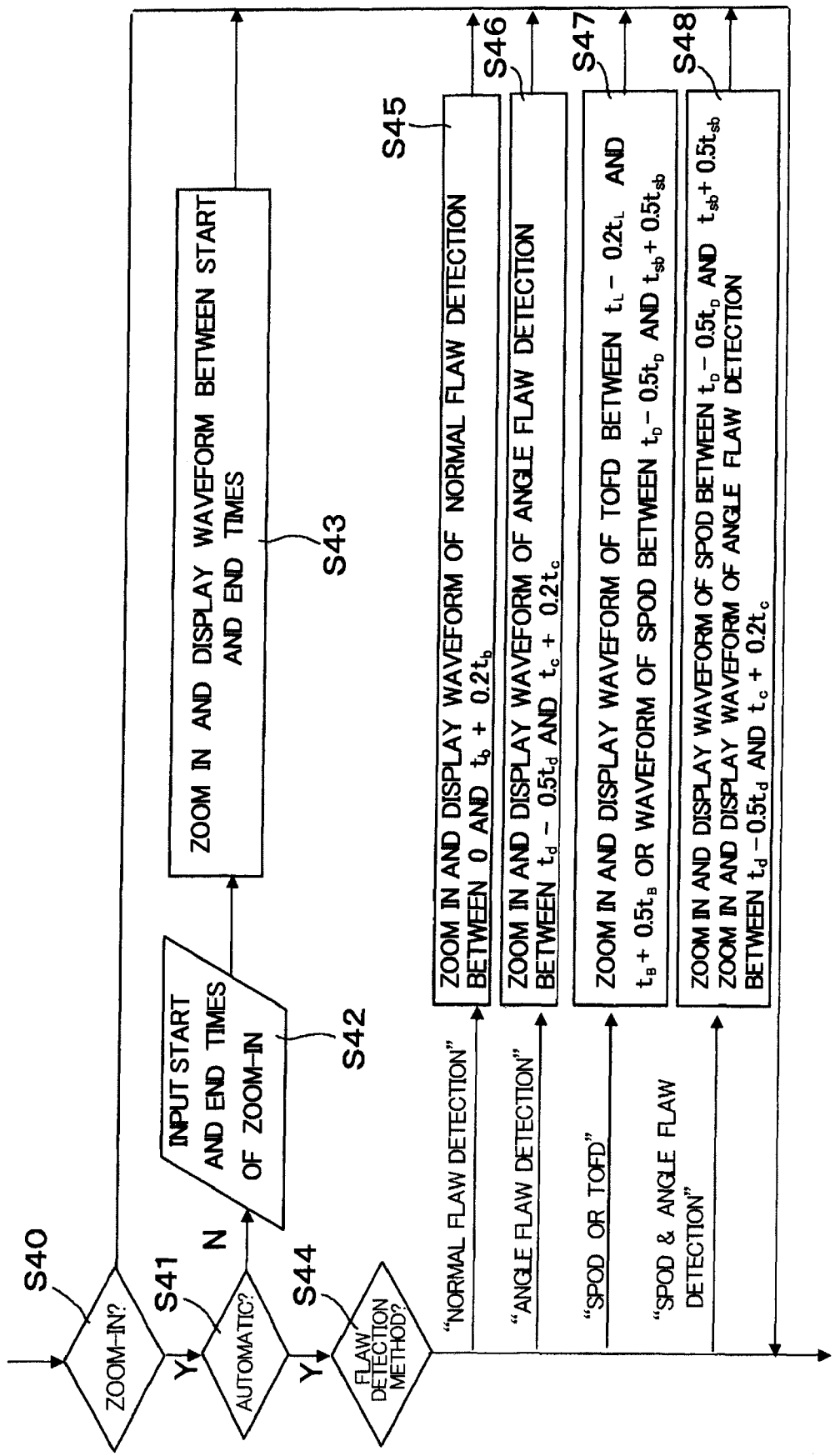
FIG. 9 is a flowchart showing an example of a waveform enlargement display process.

Next, an enlarged waveform display process will be explained (S4). FIG. 9 shows a detailed flowchart of the enlarged waveform display process. In the embodiment, time-regions before and behind the cursor 27, which was displayed in the guide display process and acts as a reference, are displayed in enlargement; hereinafter, also called a zoom in display.

When the zoom in display is selected (S40: Yes), whether it is displayed automatically or manually is selected (S41). Here, the enlarged display of a display screen, i.e., zoom in, means to display a waveform in enlargement with the cursor 27, which was displayed in the guide display process, located at the center of the waveform, which may be performed by an existing image processing art. For example, peripheral pixels (100×100 pixels) about the cursor 27 are displayed in enlargement (400×400 pixels), the display is not limited thereto. An enlarged screen may be displayed in the same window or in a different window. Further, in the embodiment, there are provided two patterns, that is, a pattern, in which the inspector manually performs the enlarged waveform display process by operating the input unit such as the mouse, and a pattern, in which the enlarged waveform display process is automatically controlled so that any of the patterns can be selected. However, the patterns are not limited thereto, and any one of the patterns may be provided.

When the enlarged waveform display process is performed manually (S41: No), a time interval for performing the enlarged display is designated. Specifically, when the start time and the end time of the time-axis are input as to the portion of a waveform which is desired to be enlarged (S42), a waveform having a designated time interval is displayed in enlargement (S43). In the embodiment, the designated time interval may be displayed by enlarging only the lateral axis a plurality of times without changing the range of the vertical axis. Note that the manual setting method is not limited the one described above, and the portion of the waveform may be displayed in enlargement by enlarging the peripheral portion thereof about the position clicked by the mouse and the like.

In the automatic setting method (S41: Yes), it is determined whether any of the flaw detection methods is selected (S44). In the embodiment, in, for example, the normal flaw detection, the waveform between 0 and $t_b + 0.2t_b$ is zoomed in and displayed (S45), in the angle flaw detection, the waveform between $t_d - 0.5t_d$ and $t_c + 0.2t_c$ is zoomed in and displayed (S46), in the SPOD method, the waveform between $t_D - 0.5t_D$ and $t_{sb} + 0.5t_{sb}$ is zoomed in and displayed (S47), and, in the angle flaw detection and the SPOD method, the waveform of the angle flaw detection between $t_d - 0.5t_d$ and $t_c + 0.2t_c$ and the SPOD waveform between $t_D - 0.5t_D$ and $t_{sb} + 0.5t_{sb}$ are enlarged and displayed (S48).

In this case, the time width for performing the enlarged display is only an example and not limited thereto, thus may be appropriately selected. Further, the time width may be set as a parameter depending on the test environment such as the specimen 26 for instance, the thickness of the specimen.

Note that, in the ultrasonic flaw detection test described above, the height of a flaw is measured from the propagation times of the respective determined waveforms. Although not shown, the ultrasonic flaw detection apparatus of the present invention has a height of flaw measurement means, and the height of a flaw is measured by a calculation formula described below. Methods of estimating a height of a flaw $h_r$ by the respective flaw detection methods of the embodiment are shown below.

A height of a flaw measurement formula of the normal flaw detection method is shown in Expression 6.

$$h_r = (t_b - t_D^N) c/2 \qquad \text{[Expression 6]}$$

where, $t_D^N$ shows the time of appearance of an edge echo.

A height of a flaw measurement formula of the angle flaw detection method is shown in Expression 7.

$$h_r = (t_c - t_D^A) c \cos \theta / 2 \qquad \text{[Expression 7]}$$

where, $t_D^A$ shows the time of appearance of an edge echo.

A height of a flaw measurement formula of the SPOD method is shown in Expression 8.

$$h_r = (t_{sb} - t_D) c_L / 2 \qquad \text{[Expression 8]}$$

As described above, according to the ultrasonic flaw detection apparatus of the embodiment, the flaw detection test can be executed by the plurality of ultrasonic flaw detection methods only by that the inspector selects the flaw detection methods displayed in the display unit 7 of the computer. Here, it is assumed that the respective flaw detection methods are executed in detail by the technology of the existing flaw detection method as described above.

Figure 11:
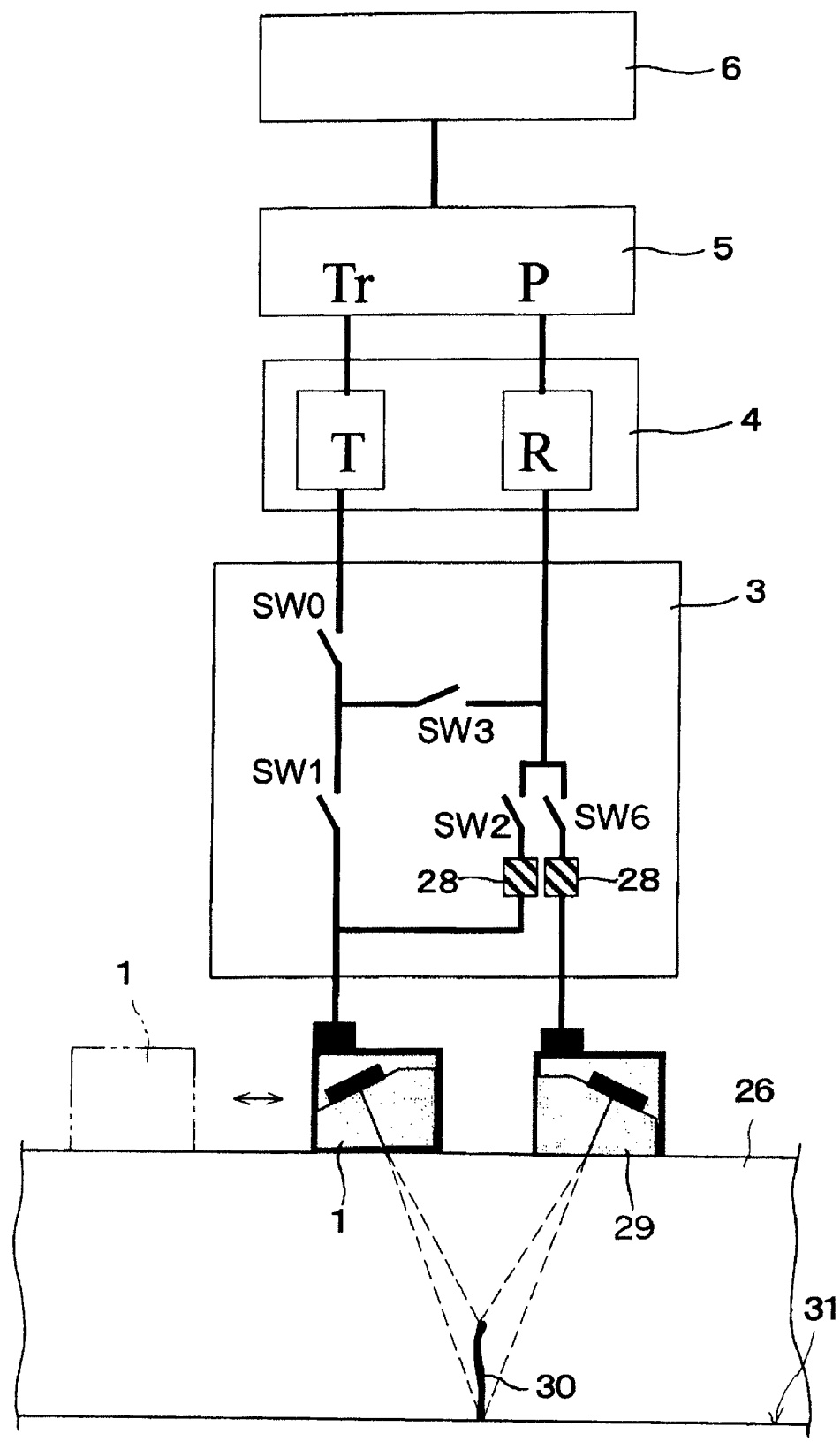
FIG. 11 is a block diagram showing an example of an ultrasonic flaw detection apparatus according to a second embodiment.

Next, FIGS. 11 and 12 show a second embodiment of the present invention. In the second embodiment, a second angle probe 29 is used in place of the normal probe 2 of the first embodiment, a TOFD method can be executed in place of the SPOD method of the first embodiment, and an ultrasonic flaw detection test can be executed by angle flaw detection method from two directions executed by two angle probes, that is, the second angle probe 29 and a first angle probe 1, the TOFD method, and a combination of the angle flaw detection and the TOFD method under the control of a switching circuit 3. Note that the switch arrangement of the switching circuit 3 is such that switches SW0 and SW1 are inserted between a transmission unit T of a pulse receiver 4 and the first angle probe 1 in series, a switch SW6 and a variable amplifier 28 are inserted in series between a reception unit R and the second angle probe 29 as well as a switch SW2 and a variable amplifier 28 for connecting the reception unit R and the first angle probe 1 are disposed beside the switch SW6, and further a switch SW3 is disposed to connect the upstream side of the switch SW1 and the upstream sides of the switches SW2 and SW6.

(1) First Mode

Figure 12A:
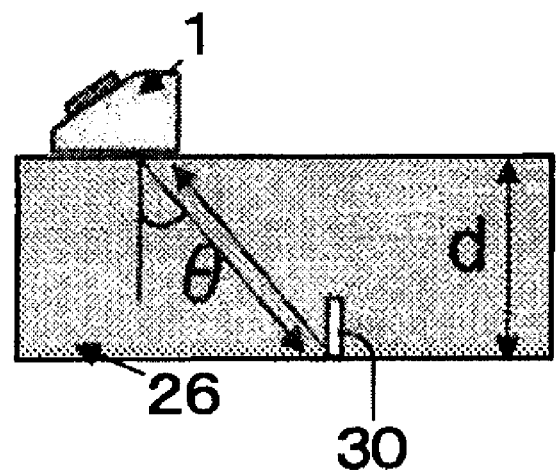
FIGS. 12A and 12B are explanatory views showing the peak times of echoes.

When the switch SW1 and the switch SW2 are turned on and the switch SW3 and the SW6 are turned off, only the first angle probe 1 is connected to the transmission unit T and the reception unit R of the pulse receiver 4, and only the first angle probe 1 transmits and receives an ultrasonic beam, thereby a so-called angle flaw detection mode for receiving an edge echo can be executed as shown in FIG. 12A.

(2) Second Mode

Figure 12B:
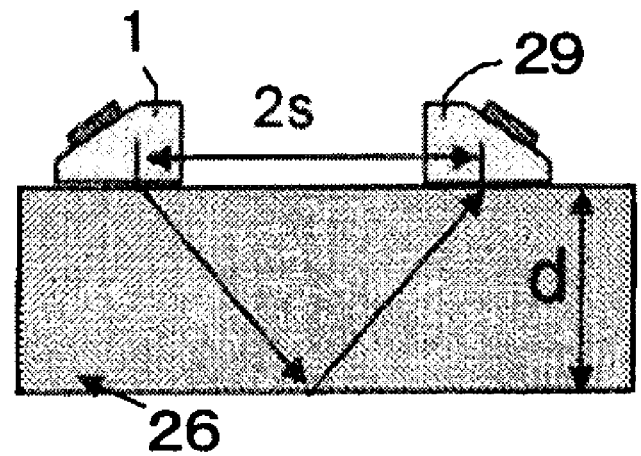

When the switches SW1 and SW6 are turned on and the switches SW2 and SW3 are turned off, the first angle probe 1 is connected to the transmission unit T of the pulse receiver 4 and the second angle probe 29 is connected to the reception unit R of the pulse receiver 4, respectively, thereby a so-called TOFD mode, in which the diffracted wave and the surface wave of the ultrasonic wave incident from the first angle probe 1 are received by the second angle probe 29, can be executed as shown in FIG. 12B.

(3) Third Mode

When the switches SW1, SW2, and SW6 are turned on and the switch SW3 is turned off, the first angle probe 1 is connected to the transmission unit T and the reception unit R of the pulse receiver 4 and the second angle probe 29 is connected to the reception unit R of the pulse receiver 4, respectively, thereby a flaw detection mode can be executed by a combination of a so-called angle flaw detection method and TOFD method in which the first angle probe 1 causes an ultrasonic wave to be incident and receives an edge echo and the second angle probe 29 receives the diffracted wave from a flaw 30.

(4) Fourth Mode

When the switches SW3 and SW6 are turned on and the switches SW1 and SW2 are turned off, only the second angle probe 29 is connected to the transmission unit T and the reception unit R of the pulse receiver 4, thereby a so-called angle flaw detection mode can be executed in which only the second angle probe 29 causes an ultrasonic wave to be incident and receives an edge echo. More specifically, the ultrasonic wave is caused to be incident from a direction different from the first angle flaw detection mode.

The parameters used in a peak time estimation process executed in the second embodiment is almost the same as those of the first embodiment. However, the gap between the probes used in the TOFD method, that is, the distance between the first angle probe 1 and the second angle probe 29 is previously set in place of the parameter "estimated height of flaw" used in the SPOD method.

The peak time estimation process in the TOFD mode which is specific to the second embodiment will now be explained. The peak time of an echo in the TOFD method means a bottom echo and a lateral echo, i.e., echo caused by a surface wave. Note that the time of appearance $t_B$ of the bottom echo in the TOFD method is determined by Expression 9.

$$t_B = 2\sqrt{s^2+d^2}/c_L + 2t_d \qquad \text{[Expression 9]}$$

Further, the time of appearance $t_L$ of the lateral echo is determined by Expression 10.

$$t_L = 2s/c_L + 2t_d \qquad \text{<Expression 10>}$$

where, s shows a value half the gap between the probes, and $c_L$ shows the sound wave of a longitudinal wave.

Further, an enlargement display process, which is executed when TOFD method is selected, displays a waveform between $t_L - 0.2 t_L$ and $t_B + 0.5 t_B$ in a zoom in mode. Here, an enlarged range is only an example, and the range is not limited to the example.

Further, a method for measuring a flaw height in the TOFD method is shown by Expression 11.

$$h_r = \sqrt{[(c_L t_2/2)^2 - s^2]} - \sqrt{[(c_L t_1/2)^2 - s^2]} \qquad \text{[Expression 11]}$$

Note that $t_1$, $t_2$ show the times at which echoes appear at upper and lower ends of a flaw, respectively.

Figure 13:
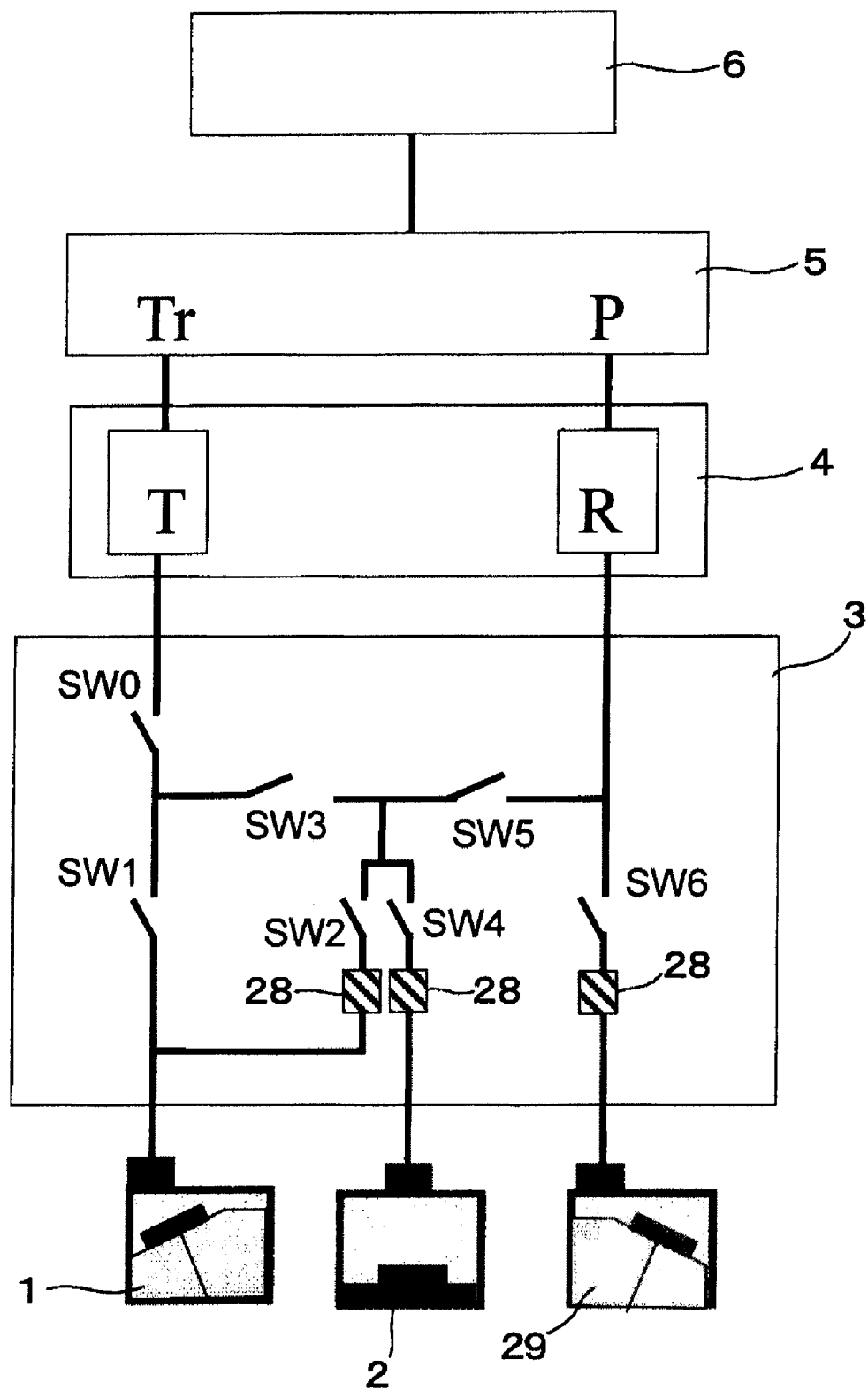
FIG. 13 is a block diagram showing an example of an ultrasonic flaw detection apparatus according to a third embodiment.

FIG. 13 shows a third embodiment of the present invention. The third embodiment realizes the first and second embodiments described above by one ultrasonic flaw detection apparatus. In the third embodiment, a first angle probe 1, a normal probe 2, and a second angle probe 29, which faces the first angle probe 1 across the normal probe 2 are selectively switched to a transmission unit T and a reception unit R of a switching circuit 3 thereby to execute all the flaw detection modes realized by the first and second embodiments, that is, the seven modes.

The switching circuit 3 of the embodiment has seven switches from SW0 to SW6. The main power supply switch SW0 and the turn-over switch SW1 are inserted between the transmission unit T of the pulse receiver 4 and the first angle probe 1 in series, whereas the switch SW6 is inserted in series between the reception unit R and the second angle probe 29. Further, the switches SW3 and SW5 are inserted in series to a conductive wire connecting the transmission unit T and the reception unit R in an upstream of the switch SW1 and upstream of the switch SW6, whereas the first angle probe 1 is connected between the switches SW3 and SW5 through the switch SW2 and a variable amplifier 28 as well as the normal probe 2 is connected between the switches SW3 and SW5 through the switch SW4 and a variable amplifier 28.

(1) First Mode

When the switches SW1, SW2, and SW5 are turned on and the switches SW3, SW4, and SW6 are turned off, an angle flaw detection mode using only the first angle probe 1 is executed.

(2) Second Mode

When the switches SW1, SW4, and SW5 are turned on and the switches SW2, SW3, and SW6 are turned off, an SPOD mode, which uses the first angle probe 1 for transmission and the normal probe 2 for reception, is executed.

(3) Third Mode

When the switches SW1, SW2, SW4, and SW5 are turned on and the switches SW3 and SW6 are turned off, a flaw detection mode, which uses the first angle probe 1 for transmission/reception and the normal probe 2 for reception, is executed by a combination of the angle flaw detection method and the SPOD method.

(4) Fourth Mode

The switches SW3, SW4, and SW5 are turned on and the switches SW1, SW2, and SW6 are turned off, a normal flaw detection mode using only the normal probe 2 is executed.

(5) Fifth Mode

When the switches SW1 and SW6 are turned on and the switches SW2, SW3, SW4, and SW5 are turned off, a TOFD mode, which uses the first angle probe 1 for transmission and the second angle probe 29 for reception, is executed.

(6) Sixth Mode

When the switches SW1, SW2, SW5, and SW6 are turned on and the switches SW3 and SW4 are turned off, a flaw detection mode, which uses the first angle probe 1 for transmission/reception and the second angle probe 29 for reception, is executed by a combination of the angle flaw detection method and the TOFD method.

(7) Seventh Mode

When the switches SW3, SW5, and SW6 are turned on and the switches SW1, SW2, and SW4 are turned off, an angle flaw detection mode, which uses only the second angle probe 29, is executed.

That is, according to the third ultrasonic flaw detection apparatus and the ultrasonic flaw detection program, the various ultrasonic flaw detection methods such as the angle flaw detection method in the different direction, the normal flaw detection method, the TOFD method, the SPOD method and the combinations of these methods can be simply controlled by switching the switch patterns of the switching circuit.

Although the embodiments described above are preferable examples of the present invention, the present invention is by no means limited thereto and may be variously modified and embodied within a scope which does not depart from the gist of the present invention. For example, the ultrasonic flaw detection apparatus of the present invention can also be used for a phased array method using, for example, a phased array probe. Further, the circuit arrangement of the illustrated switching circuit such as the positions of the switches is only an example and is not limited thereto. That is, any circuit arrangement may be used as long as the probes are connected to and disconnected from the pulse receiver 4 by turning on and off switches.

The invention claimed is:

1. An ultrasonic flaw detection apparatus comprising: an angle probe, a normal probe, and a switching circuit for permitting connection of the angle probe and the normal probe to a transmission unit and a reception unit of a flaw detector to be switched, wherein the switching circuit selects an angle flaw detection mode for transmitting and receiving an ultrasonic beam only by the angle probe, an SPOD mode for transmitting the ultrasonic beam by the angle probe and receiving a diffracted wave propagating on a flaw detection surface above a flaw by the normal probe, a mode for simultaneously executing the angle flaw detection mode and the SPOD mode for transmitting the ultrasonic beam by the angle probe and receiving a reflected wave by the angle probe as well as receiving the diffracted wave propagating on the flaw detection surface above the flaw by the normal probe, and a normal flaw detection mode for transmitting and receiving the ultrasonic beam only by the normal probe.

2. An ultrasonic flaw detection apparatus comprising: a first angle probe, a second angle probe disposed by facing the first angle probe, and a switching circuit for permitting connection of the respective angle probes to a transmission unit and a reception unit of a flaw detector to be switched, wherein the switching circuit selects an angle flaw detection mode for transmitting and receiving an ultrasonic beam only by the first angle probe, a TOFD mode for transmitting the ultrasonic beam by the first angle probe and receiving a surface wave and a diffracted wave by the second angle probe, a mode for simultaneously executing the angle flaw detection mode and the TOFD mode for transmitting the ultrasonic beam by the first angle probe and receiving a reflected wave by the first angle probe as well as receiving the surface wave and the diffracted wave by the second angle probe, and an angle flaw detection mode for transmitting and receiving the ultrasonic beam only by the second angle probe.

3. An ultrasonic flaw detection apparatus comprising: a first angle probe, a normal probe, a second angle probe disposed by facing the first angle probe across the normal probe, and a switching circuit for permitting connection of the respective angle probes to a transmission unit and a reception unit of a flaw detector to be optionally switched, wherein the switching circuit selects an angle flaw detection mode for transmitting and receiving an ultrasonic beam only by the first angle probe, an SPOD mode for transmitting the ultrasonic beam by the first angle probe and receiving a diffracted wave propagating on a flaw detection surface above a flaw by the normal prove, a mode for simultaneously executing the angle flaw detection mode and the SPOD mode for transmitting the ultrasonic beam by the first angle probe and receiving a reflected wave by the first normal probe as well as receiving the diffracted wave by the normal probe, a normal flaw detection mode for transmitting and receiving the ultrasonic beam only by the normal probe, a TOFD mode for transmitting the ultrasonic beam by the first angle probe and receiving a surface wave and the diffracted wave by the second angle probe, a mode for simultaneously executing the angle flaw detection mode and the TOFD mode for transmitting the ultrasonic beam by the first angle probe and receiving the reflected wave by the first angle probe as well as receiving the surface wave and the diffracted wave by the second angle probe, and an angle flaw detection mode for transmitting and receiving an ultrasonic beam only by the second angle probe.

4. The ultrasonic flaw detection apparatus according to claim 1, comprising a peak time estimation means for estimating the time of appearance of the peak of an echo from parameters of a specimen previously set according to a flaw detection mode selected by the switching circuit, and a guide display means for displaying the position of appearance of the peak of the echo estimated by the peak time estimation means to the time-axis of a display unit for displaying a detected peak of echo by a cursor.

5. The ultrasonic flaw detection apparatus according to claim 4, comprising an enlarged waveform display means for displaying the region of a previously designated range to the display unit in enlargement with the displayed position of the cursor located at the center of the region.

6. The ultrasonic flaw detection apparatus according to claim 4, wherein the guide display means changes the background color of a waveform of the display unit depending on which of the flaw detection modes is selected.

7. The ultrasonic flaw detection apparatus according to claim 4, which causes the display unit to simultaneously display the waveforms formed by the plurality of ultrasonic flaw detection methods when an ultrasonic flaw detection test is executed to the specimens by the plurality of ultrasonic flaw detection methods.

8. An ultrasonic flaw detection program operating on a computer, the ultrasonic flaw detection program causing the computer, which controls a switching circuit for arbitrarily switching connection of an angle probe and a normal probe to a transmission unit and a reception unit of a pulse receiver, to execute a circuit selection process for controlling switching of the switching circuit according to a flaw detection mode selected, by an input unit, from an angle flaw detection mode for transmitting and receiving an ultrasonic beam only by the angle probe, an SPOD mode for transmitting the ultrasonic beam by the angle probe and receiving a diffracted wave propagating on a flaw detection surface above a flaw by the normal probe, a mode for simultaneously executing the angle flaw detection method and the SPOD method for transmitting the ultrasonic beam by the angle probe and receiving a reflected wave by the angle probe as well as receiving the diffracted wave propagating on the flaw detection surface above the flaw by the normal probe, and a normal flaw detection mode for transmitting and receiving the ultrasonic beam only by the normal probe.

9. An ultrasonic flaw detection program operating on a computer, the ultrasonic flaw detection program causing the computer, which controls a switching circuit for arbitrarily switching connection of a first angle probe and a second angle probe disposed by facing the first angle probe to a transmission unit and a reception unit of a pulse receiver, to execute a circuit selection process for controlling switching of the switching circuit according to a flaw detection mode selected, by an input unit, from an angle flaw detection mode for transmitting and receiving an ultrasonic beam only by the first angle probe, a TOFD mode for transmitting the ultrasonic beam by the first angle probe and receiving a surface wave and the diffracted wave by the second angle probe, a mode for simultaneously executing the angle flaw detection method and the TOFD method for transmitting the ultrasonic beam by the first angle probe and receiving a reflected wave by the first angle probe as well as receiving the surface wave and the diffracted wave by the second angle probe, and an angle flaw detection mode for transmitting and receiving the ultrasonic beam only by the second angle probe.

10. An ultrasonic flaw detection program operating on a computer, the ultrasonic flaw detection program causing the computer, which controls a switching circuit for arbitrarily switching connection of a first angle probe, a normal probe, and a second angle probe disposed by facing the first angle probe to a transmission unit and a reception unit of a pulse receiver, to execute a circuit selection process for controlling switching of the switching circuit according to a flaw detection mode selected, by an input unit, from an angle flaw detection mode for transmitting and receiving an ultrasonic beam only by the angle probe, an SPOD mode for transmitting the ultrasonic beam by the first angle probe and receiving a diffracted wave propagating on a flaw detection surface above a flaw by the normal probe, a mode for simultaneously executing the angle flaw detection method and the SPOD method for transmitting the ultrasonic beam by the first angle probe and receiving a reflected wave by the first angle probe as well as receiving the diffracted wave by the angle probe, a normal flaw detection mode for transmitting and receiving the ultrasonic beam only by the normal probe, a TOFD mode for transmitting the ultrasonic beam by the first angle probe and receiving a surface wave and the diffracted wave by the second angle probe, a mode for simultaneously executing the angle flaw detection method and the TOFD method for transmitting the ultrasonic beam by the first angle probe and receiving the reflected wave by the first angle probe as well as receiving the surface wave and the diffracted wave by the second angle probe, and an angle flaw detection mode for transmitting and receiving the ultrasonic beam only by the second angle probe.

11. The ultrasonic flaw detection program according to claim 8, wherein a memory unit previously stores parameters of respective selected flaw detection modes, which are necessary to estimate the time of appearance of the peak of an echo detected in a selected flaw detection mode, and a computer is caused to execute a peak time estimation process for causing an arithmetic operation unit to calculate the time of appearance of the peak of an echo using the parameters from the memory unit as input values and a guide display process for displaying a cursor, which shows the position of appearance of the peak of the echo estimated by the peak time estimation process, to the time-axis of the detected echo displayed on a display unit.

* * * * *